United States Patent
Fu et al.

(10) Patent No.: US 10,117,626 B2
(45) Date of Patent: Nov. 6, 2018

(54) APPARATUS AND METHOD FOR PILE-UP CORRECTION IN PHOTON-COUNTING DETECTOR

(71) Applicant: General Electric Company, Schenectady, NY (US)

(72) Inventors: Geng Fu, Niskayuna, NY (US); Peter Michael Edic, Niskayuna, NY (US); Brian David Yanoff, Niskayuna, NY (US); Jianjun Guo, Ballston Spa, NY (US); Vladimir A. Lobastov, Niskayuna, NY (US); Yannan Jin, Niskayuna, NY (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 219 days.

(21) Appl. No.: 14/868,826

(22) Filed: Sep. 29, 2015

(65) Prior Publication Data

US 2017/0086761 A1  Mar. 30, 2017

(51) Int. Cl.
*A61B 6/03* (2006.01)
*A61B 6/00* (2006.01)

(52) U.S. Cl.
CPC .......... *A61B 6/4241* (2013.01); *A61B 6/032* (2013.01); *A61B 6/4208* (2013.01); *A61B 6/4233* (2013.01); *A61B 6/4435* (2013.01); *A61B 6/4441* (2013.01); *A61B 6/54* (2013.01)

(58) Field of Classification Search
CPC ..... A61B 6/032; A61B 6/4208; A61B 6/4233; A61B 6/4241; A61B 6/4435; A61B 6/4441; A61B 6/54

USPC .......... 378/19, 98.8, 98.9, 98.11; 250/370.09
See application file for complete search history.

(56) References Cited

U.S. PATENT DOCUMENTS

| | | | | |
|---|---|---|---|---|
| 5,943,388 A | * | 8/1999 | Tümer | G01V 5/0041 378/98.11 |
| 6,169,287 B1 | * | 1/2001 | Warburton | G01T 1/2928 250/370.09 |
| 6,509,565 B2 | * | 1/2003 | Nygard | G01T 1/17 250/336.1 |
| 7,149,278 B2 | * | 12/2006 | Arenson | A61B 6/4241 378/19 |
| 7,208,739 B1 | | 4/2007 | Yanoff et al. | |
| 7,260,174 B2 | | 8/2007 | Hoffman et al. | |
| 7,263,167 B2 | * | 8/2007 | Walter | A61B 6/032 378/116 |
| 7,339,175 B1 | * | 3/2008 | Drummond | G01T 1/2928 250/370.01 |
| 7,361,881 B2 | * | 4/2008 | Spartiotis | G01T 1/2928 250/208.1 |

(Continued)

*Primary Examiner* — Allen C. Ho
(74) *Attorney, Agent, or Firm* — GE Global Patent Operation; Pabitra Chakrabarti

(57) ABSTRACT

Some embodiments are associated with an input signal comprising a first and a second photon event incident on a photon-counting semiconductor detector. A relatively slow charge collection shaping amplifier may receive the input signal and output an indication of a total amount of energy associated with the superposition of the first and second events. A relatively fast charge collection shaping amplifier may receive the input signal and output an indication that is used to allocate a first portion of the total amount of energy to the first event and a second portion of the total amount of energy to the second event.

18 Claims, 10 Drawing Sheets

(56) References Cited

U.S. PATENT DOCUMENTS

| | | | |
|---|---|---|---|
| 7,372,031 B2* | 5/2008 | Cerwin | G01J 1/02 250/336.1 |
| 7,433,443 B1* | 10/2008 | Tkaczyk | A61B 6/032 378/19 |
| 7,480,362 B2* | 1/2009 | Carmi | A61B 6/032 378/19 |
| 7,488,945 B2 | 2/2009 | Li et al. | |
| 7,512,210 B2* | 3/2009 | Possin | A61B 6/032 250/370.09 |
| 7,514,688 B2* | 4/2009 | Broennimann | H01L 27/14661 250/370.11 |
| 7,532,703 B2* | 5/2009 | Du | A61B 6/032 378/116 |
| 7,547,889 B2* | 6/2009 | Lehmann | G01T 1/17 250/370.09 |
| 7,573,040 B2* | 8/2009 | Tkaczyk | G01T 1/249 250/370.09 |
| 7,582,878 B2* | 9/2009 | Shahar | G01T 1/2928 250/370.09 |
| 7,586,168 B2* | 9/2009 | Raynor | H04N 3/155 257/431 |
| 7,613,274 B2* | 11/2009 | Tkaczyk | A61B 6/032 378/19 |
| 7,615,753 B2* | 11/2009 | Audebert | G01T 1/17 250/370.07 |
| 7,615,755 B2* | 11/2009 | Coello | H04N 3/155 250/370.01 |
| 7,634,061 B1* | 12/2009 | Tümer | G01T 1/247 378/62 |
| 7,646,845 B2* | 1/2010 | Lecomte | A61B 6/032 378/19 |
| 7,696,483 B2* | 4/2010 | Tkaczyk | G01T 1/171 250/370.06 |
| 7,738,631 B2* | 6/2010 | Rundle | G01N 33/12 250/370.09 |
| 7,760,123 B2* | 7/2010 | Rao | G06G 7/18 341/155 |
| 7,829,860 B2* | 11/2010 | Nygard | G01T 1/2018 250/370.09 |
| 7,894,576 B2* | 2/2011 | Carmi | G01T 1/2985 250/370.09 |
| 7,902,976 B2* | 3/2011 | Doughty | G01T 1/026 250/370.1 |
| 7,916,836 B2 | 3/2011 | Tkaczyk et al. | |
| 7,943,907 B2* | 5/2011 | Eversmann | G01T 1/17 250/395 |
| 7,956,332 B2* | 6/2011 | Burr | G01T 1/20 250/361 R |
| 8,044,681 B2* | 10/2011 | Rao | A61B 6/037 250/208.1 |
| 8,159,286 B2* | 4/2012 | Rao | G01T 1/2985 327/337 |
| 8,198,577 B2* | 6/2012 | Dierickx | G01T 1/247 250/214 DC |
| 8,212,220 B2* | 7/2012 | Lerch | G01T 1/161 250/366 |
| 8,243,874 B2* | 8/2012 | Carmi | G01T 1/2985 250/366 |
| 8,350,221 B2* | 1/2013 | Steadman Booker | G01T 1/17 250/336.1 |
| 8,378,307 B2* | 2/2013 | Baeumer | G01T 1/2985 250/362 |
| 8,378,310 B2* | 2/2013 | Bornefalk | G06T 11/005 250/370.01 |
| 8,384,038 B2* | 2/2013 | Guo | G01T 1/247 250/370.09 |
| 8,415,635 B2* | 4/2013 | Marks | G01T 1/171 250/370.09 |
| 8,426,828 B2* | 4/2013 | Dierickx | G01J 1/44 250/371 |
| 8,440,957 B2* | 5/2013 | Dierickx | G01T 1/247 250/214 R |
| 8,488,854 B2* | 7/2013 | Arenson | G06T 11/005 378/1 |
| 8,533,137 B2* | 9/2013 | Turbin | G01T 1/2957 706/17 |
| 8,610,081 B2* | 12/2013 | Rao | G01T 1/247 250/394 |
| 8,680,474 B2* | 3/2014 | Soh | H01L 27/14609 250/370.09 |
| 8,729,485 B2* | 5/2014 | Soh | H04N 5/378 250/370.09 |
| 8,766,198 B2* | 7/2014 | Dinapoli | G01T 1/243 250/370.01 |
| 8,772,730 B2* | 7/2014 | Han | G01T 1/247 250/363.01 |
| 8,816,290 B2* | 8/2014 | Hamlin | G01T 1/17 250/370.08 |
| 8,927,937 B2* | 1/2015 | Schwarzman | G01T 1/24 250/370.01 |
| 8,941,076 B2* | 1/2015 | Abraham | G01T 1/171 250/336.1 |
| 8,988,267 B1* | 3/2015 | Kimura | H04N 5/378 341/155 |
| 9,000,385 B2* | 4/2015 | Dror | G01T 1/171 250/370.06 |
| 9,029,793 B2* | 5/2015 | Spartiotis | H04N 5/32 250/370.09 |
| 9,052,266 B2* | 6/2015 | Miyazaki | A61B 6/4241 |
| 9,057,788 B2* | 6/2015 | Abraham | G01T 1/1647 |
| 9,101,273 B2* | 8/2015 | Gagnon | G01T 1/24 |
| 9,103,924 B2* | 8/2015 | Nygard | G01T 1/247 |
| 9,121,949 B2* | 9/2015 | Lerche | G01T 1/17 |
| 9,121,955 B2* | 9/2015 | Schmitt | G01T 1/247 |
| 9,128,195 B2* | 9/2015 | Soh | H04N 5/32 |
| 9,160,939 B2* | 10/2015 | Funaki | H03M 1/145 |
| 9,164,183 B2* | 10/2015 | Kraft | G01T 1/40 |
| 9,176,238 B2* | 11/2015 | Herrmann | G01T 1/17 |
| 9,220,469 B2* | 12/2015 | Jin | A61B 6/4241 |
| 9,291,724 B2* | 3/2016 | Proksa | G01T 1/24 |
| 9,294,700 B2* | 3/2016 | Nishihara | H01L 27/14603 |
| 9,310,490 B2* | 4/2016 | Abraham | G01T 1/17 |
| 9,310,495 B2* | 4/2016 | Spartiotis | G01T 1/247 |
| 9,335,424 B2* | 5/2016 | Herrmann | G01T 1/171 |
| 9,354,331 B2* | 5/2016 | Sagoh | A61B 6/032 |
| 9,416,022 B2* | 8/2016 | Saito | C01G 29/00 |
| 9,417,339 B2* | 8/2016 | Spahn | G01T 1/247 |
| 9,444,344 B2* | 9/2016 | Kim | G01T 1/247 |
| 9,476,993 B2* | 10/2016 | Wang | G01T 1/17 |
| 9,504,439 B2* | 11/2016 | Yi | A61B 6/5205 |
| 9,513,175 B2* | 12/2016 | Prendergast | G01T 1/247 |
| 9,535,167 B2* | 1/2017 | Proksa | G01T 1/171 |
| 9,535,174 B2* | 1/2017 | Engel | G01T 1/249 |
| 9,588,239 B2* | 3/2017 | Abraham | G01T 1/247 |
| 9,603,577 B2* | 3/2017 | Oh | A61B 6/484 |
| 9,664,797 B2* | 5/2017 | Roessl | G01T 1/171 |
| 9,678,220 B2* | 6/2017 | Herrmann | G01T 1/17 |
| 9,759,822 B2* | 9/2017 | Daerr | G01T 1/17 |
| 9,778,379 B2* | 10/2017 | Sagoh | G01T 1/208 |
| 9,784,854 B2* | 10/2017 | Blevis | G01T 1/2928 |
| 9,829,377 B2* | 11/2017 | Steadman Booker | G01J 1/44 |
| 9,841,389 B2* | 12/2017 | Tamura | G01N 23/046 |
| 9,854,656 B2* | 12/2017 | Göderer | H05G 1/58 |
| 9,885,674 B2* | 2/2018 | Ouvrier-Buffet | G01N 23/087 |
| 9,952,164 B2* | 4/2018 | Wiedmann | G01N 23/046 |
| 9,971,047 B2* | 5/2018 | Tamura | G01T 1/2985 |
| 2007/0076848 A1 | 4/2007 | Walter et al. | |
| 2010/0193700 A1 | 8/2010 | Herrmann et al. | |
| 2013/0049151 A1 | 2/2013 | Lobastov et al. | |
| 2014/0314211 A1 | 10/2014 | Zou et al. | |
| 2015/0078512 A1 | 3/2015 | Goderer et al. | |

* cited by examiner

APPARATUS AND METHOD FOR PILE-UP CORRECTION IN PHOTON-COUNTING DETECTOR

BACKGROUND

The invention relates to detectors and, more particularly, to an apparatus and method for pile-up correction in a photon-counting detector for medical imaging and similar applications.

X-ray computed tomography imaging, also referred to as Computed Tomography (CT) or Computed Axial Tomography (CAT), employs computer-processed X-ray projections to generate images of the interior of an object of interest. These systems generally successively emit and detect photons in the X-ray energy range, directed toward an object, so as to generate a plurality of consecutive-projection data of the object's contents. The projection data may then be used to generate a three-dimensional image of the inside of the object. The three-dimensional image may be used for diagnostic and therapeutic purposes in various medical disciplines, but may also be used in a wide variety of other contexts, such as baggage inspection and industrial part inspection.

CT photon-counting detection systems, and certain X-ray detection systems in general, may seek to improve image quality by counting a number of photons that are received at a radiation detector. Such photon-counting detectors may, for example, reduce or eliminate electronic noise and/or provide improved energy-resolving capabilities. In many clinical applications, however, the photon flux generated by the X-ray tube of diagnostic CT is much higher than what currently available photon-counting detectors can accommodate. As a result, a photon-counting detector may experience a "pile-up" condition where X-ray photons arrive at the detector at such a rate that it may be difficult to determine which X-ray detection event is associated with each particular photon. Pile up causes error in both the estimation of the number and energy of the detected photons; these errors may cause the quality of a generated image to be degraded.

Therefore, it would be desirable to design an apparatus and method to provide an accurate estimate of both the count and energy of detected X-ray photons with a photon-counting detector in a practical manner.

BRIEF DESCRIPTION

According to some embodiments, a detection system may receive an input signal associated with a superposition of a first and a second event in a photon-counting semiconductor detector. A relatively slow charge collection shaping amplifier may receive the input signal and output an indication of a total amount of energy associated with the combined first and second events. A relatively fast charge collection shaping amplifier may receive the input signal and output an indication that is used to allocate a first portion of the total amount of detected energy to the first event and a second portion of the total amount of detected energy to the second event. Note that while some embodiments are described herein with respect to two photon-counting detection events, additional embodiments may be associated with additional photon-counting detection events (i.e., three or more photon-counting detection events).

Some embodiments comprise: means for receiving an input signal associated with a superposition of a first and a second event in a photon-counting semiconductor detector; means for generating, by a relatively slow charge collection shaping amplifier based on the input signal, an indication of a total amount of energy associated with the first and second events; and means for allocating, in accordance with information from a relatively fast charge collection shaping amplifier based on the input signal, a first portion of the total amount of energy to the first event and a second portion of the total amount of energy to the second event.

A technical effect of some embodiments described herein may be an improved and accurate capturing of information pertaining to X-ray detection events (achieved, e.g., via a more accurate photon-counting detector). Embodiments may be associated with systems and/or computer-readable medium storing instructions to perform any of the methods described herein.

FIGURES

DETAILED DESCRIPTION

As used herein, the "energy" of an X-ray photon is directly related to the associated electromagnetic "frequency" of the photon. A "flux" is a relation, such as a ratio, between the number of photons passing through a fixed region over a period of time. In some embodiments, the emission flux is a rate of photon emission in photons per steradian per second and detection flux is a rate of photon incidence on a detector in photons per second, wherein the detector has a certain size and is positioned at a certain distance from the source of X-ray emission. Increasing current at the X-ray source will increase the number of emitted photons, while increasing the voltage at the X-ray source will increase the maximum energy of the emitted photons, and may increase the number of emitted photons.

Figure 1A:
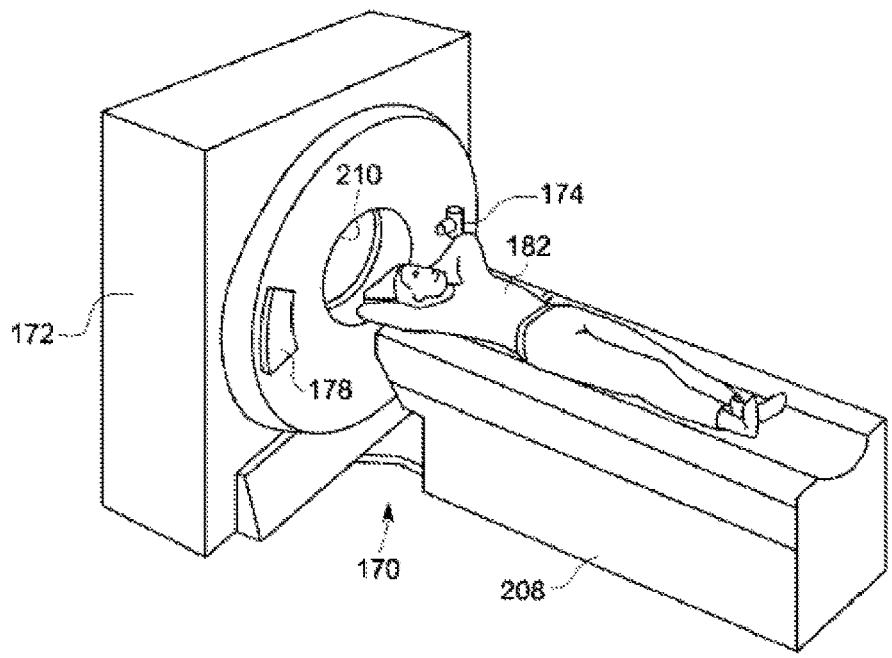
FIG. 1A is pictorial view of a Computed Tomography ("CT") imaging system in connection with which various embodiments may be implemented.
Figure 1B:
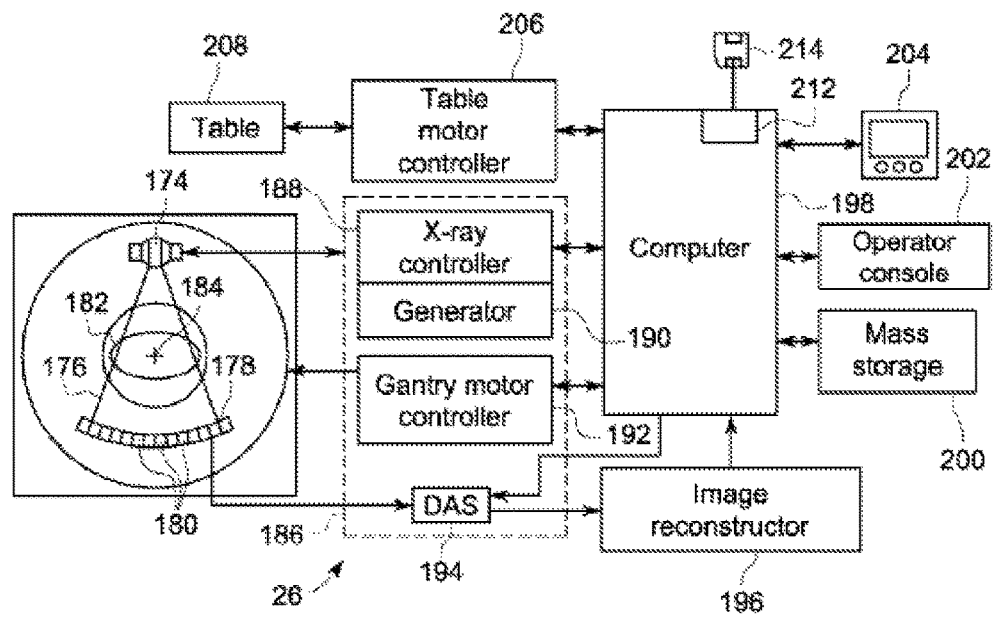
FIG. 1B is a block schematic diagram of the CT imaging system of FIG. 1A.

FIG. 1A is a pictorial view of a CT imaging system 170. FIG. 1B is a block schematic diagram of the system 170 illustrated in FIG. 1A. In the exemplary embodiment, the CT imaging system 170 is shown as including a gantry 172 representative of a "third generation" CT imaging system, where the X-ray source 174 and the X-ray detector array 178 rotate about the patient 182 or object to be imaged. The gantry 172 comprises an X-ray source 174 that emits a fan beam or cone beam 176 of X-rays toward a detector array 178, positioned on the opposite side of gantry 172. In some embodiments, X-ray source 174 is a Bremsstrahlung X-ray source. Although mentioned in terms of a "third generation" CT imaging system, the systems and methods described herein equally apply to alternate generations of CT imaging systems. Furthermore, alternate configurations of the CT imaging system are envisioned, i.e. configurations where the X-ray source 174 and X-ray detector array 178 are held stationary, and the patient 182 to be imaged is rotated.

The detector array 178 may be formed by a plurality of detector rows (not shown) including a plurality of detector elements 180 that together sense the projected X-ray beams that pass through an object, such as a medical patient 182, a piece of luggage, or an industrial part. Each detector element 180 may produce an electrical signal that represents the intensity of an impinging X-ray radiation beam 176 and hence is indicative of the attenuation of the X-ray radiation beam 176 as it passes through object or patient 182. In a photon-counting detector, the intensity may correspond to the number of incident photons impinging upon the detector element 180. A CT imaging system 170 having a multi-slice detector array 178 may be capable of generating a plurality of images representative of a volume of patient 182. Each image of the plurality of images corresponds to a separate "slice" of the volume. The "thickness" or aperture of the slice is dependent upon the height of the detector rows.

During a scan to acquire X-ray projection data, a rotating section within the gantry 172 and the components mounted thereon rotate about a center of rotation 184. FIG. 1B is a block schematic diagram 26 showing only a single row of detector elements 180 (i.e., a single detector row). However, the multi-slice detector array 178 may include a plurality of parallel detector rows of detector elements 180 such that projection data corresponding to cone-beam geometry can be acquired simultaneously during a scan.

Rotation of components within the gantry 172 and the operation of X-ray source 174 may be governed by a control mechanism 186. The control mechanism 186 includes an X-ray controller 188 and generator 190 that provides power and timing signals to the X-ray source 174 and a gantry motor controller 192 that controls the rotational speed and position of rotating portion of gantry 172. A Data Acquisition System ("DAS") 194 in the control mechanism 186 samples analog data from detector elements 180 and converts the analog signals to digital signals for subsequent processing. According to some embodiments, the DAS 194 might be located within the gantry 172. An image reconstructor 196 receives sampled and digitized measurement data from the DAS 194 and performs high-speed image reconstruction. The reconstructed image is applied as an input to a computer 198 that stores the image in a mass storage device 200. Although shown as a separate device, image reconstructor 196 may be special hardware located inside computer 198 or software executing within computer 198.

The computer 198 also receives commands and scanning parameters from an operator via a console 202 that has a keyboard and/or other user-input device(s). An associated display system 204 allows the operator to observe the reconstructed image and other data from the computer 198. The operator supplied commands and parameters may be used by the computer 198 to provide control signals and information to the DAS 194, X-ray controller 188, generator 190 and gantry motor controller 192. In addition, the computer 198 operates a table motor controller 206 that controls a motorized table 208 to position the patient 182 in the gantry 172. The motorized table 208 moves portions of the patient 182 through a gantry opening 210.

In one embodiment, the computer 198 includes a device 212, for example, a floppy disk drive, CD-ROM drive, DVD-ROM drive, or a solid state hard drive for reading instructions and/or data from a computer-readable medium 214, such as a floppy disk, CD-ROM, or DVD. It should be understood that other types of suitable computer-readable memory are recognized to exist (e.g., CD-RW and flash memory, to name just two), and that this description is not intended to exclude any of these devices. In another embodiment, the computer 198 executes instructions stored in firmware (not shown). Generally, a processor in at least one of the DAS 194, image reconstructor 196, and computer 198 shown in FIG. 1B may be programmed to execute control commands to perform switching as described in more detail herein. The switching is not limited to practice in the CT imaging system 170 and can be utilized in connection with many other types and variations of imaging systems. In one embodiment, the computer 198 is programmed to perform different functions to switch the switching devices described herein, accordingly, as used herein, the term computer is not limited to just those integrated circuits referred to in the art as computers, but broadly refers to computers, processors, microcontrollers, microcomputers, programmable logic controllers, application specific integrated circuits, and other programmable circuits.

Figure 2:
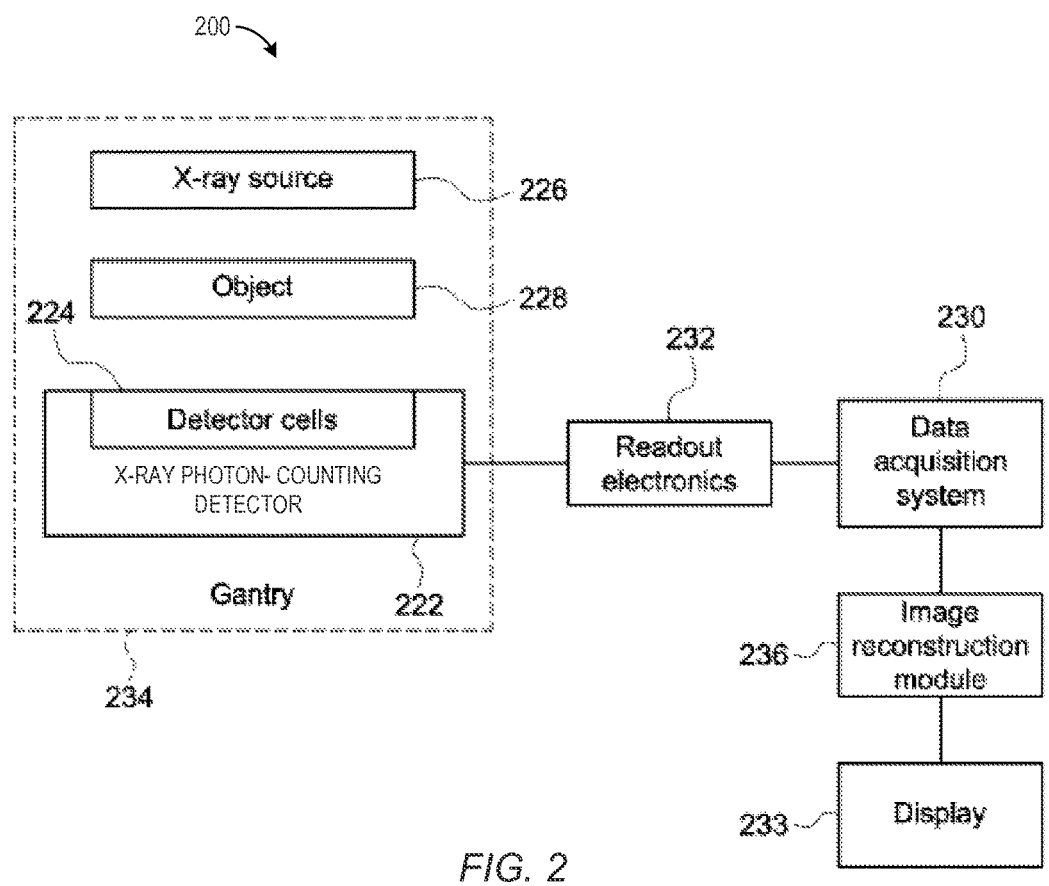
FIG. 2 is a schematic block diagram of readout electronics and an X-ray imaging system in connection with which various embodiments may be implemented.

FIG. 2 illustrates an X-ray imaging system 200 in which various embodiments may be implemented. The X-j imaging system 200 generally includes an X-ray photon-counting detector 222 having an array of detector cells 224 defining a scan area, and an X-ray source 226. Detector cells 224 may be the same as the detector elements 180 of the CT scanner of FIG. 1B in some embodiments. An object 228, such as a patient or object, is positioned between the X-ray source 226 and the X-ray photon-counting detector 222, which may be one or more detectors or detector modules. However, the X-ray imaging system 200 may also scan other objects, such as in an industrial inspection application. The X-ray imaging system 200 also includes a data acquisition system 230 and readout electronics 232. Although shown separately in FIG. 2, the readout electronics 232 may reside within the X-ray photon-counting detector 222 or the data acquisition system 230. Further note that, according to some embodiments, the data acquisition system 230 might be located within a gantry 234.

In one embodiment, the X-ray photon-counting detector(s) 222 may be flat-panel detection systems such as an amorphous-silicon flat-panel detector or other type of digital X-ray image detector, such as a direct-conversion detector as known to those skilled in the art. In another embodiment, the X-ray photon-counting detector(s) 222 may include a scintillator having a screen that is positioned in front of the X-ray photon-counting detector(s) 222. Some embodiments may be associated with a room-temperature semiconductor detector, such as a cadmium-telluride (CdTe), cadmium-zinc-telluride (CZT), and/or a mercuric-iodide (HgI) detector.

It should be noted that the X-ray imaging system 200 may be implemented as a non-mobile or mobile imaging system. Moreover, the X-ray imaging system 200 may be provided in different configurations. For example, the image data may be generated with one or more X-ray sources 226 positioned at discrete foci along an arc, line, one-dimensional path, or two-dimensional surface (not shown) about the object to generate the imaging information using computed tomography or tomosynthesis procedures and processes (or maybe with the X-ray source in a radiographic configuration). In other embodiments, the X-ray source 226 and the X-ray photon-counting detector 222 are both mounted at opposite ends of a gantry 234, which may be a C-arm that rotates about the object 228. The rotatable C-arm is a support structure that allows rotating the X-ray source 226 and the X-ray photon-counting detector 222 around the object 228 along a substantially circular arc, to acquire a plurality of projection data of the object 228 at different angles (e.g., different views or projections) that are typically less than 360 degrees, but may comprise a full rotation in some embodiments. Although described in reference to X-ray and CT imaging systems, the systems and methods described herein are directly applicable to any data acquisition system 230 where improved fidelity of X-ray detection events (both count and energy) is desired.

In operation, the object 228 is positioned in the X-ray imaging system 200 for performing an imaging scan. For example, the X-ray source 226 may be positioned above, below or around the object 228. For example, the X-ray source 226 (and the X-ray photon-counting detector(s) 222) may be moved between different positions around the object 228 using the gantry 234. X-rays are transmitted from the X-ray source 226 through the object 228 to the X-ray photon-counting detector(s) 222, which detect X-rays impinging thereon. The readout electronics 232 may include a Reference and Regulation Board ("RRB") or other data collection unit. The RRB may accommodate and connect data modules to transfer data (e.g., a plurality of views or projections) from the X-ray photon-counting detector(s) 222 to the data acquisition system 230. Thus, the readout electronics 232 transmit the data from the X-ray photon-counting detector(s) 222 to the data acquisition system 230. The data acquisition system 230 forms an image from the data and may store, display (e.g., on a display similar to display 233), and/or transmit the image. For example, the various embodiments may include an image reconstruction module 236, which may be implemented in hardware, software, or a combination thereof, that allows the data acquisition system 230 to reconstruct images using X-ray data (e.g., radiographic or tomosynthesis data) acquired from the X-ray photon-counting detector(s) 222 and as described in more detail herein.

Figure 3:
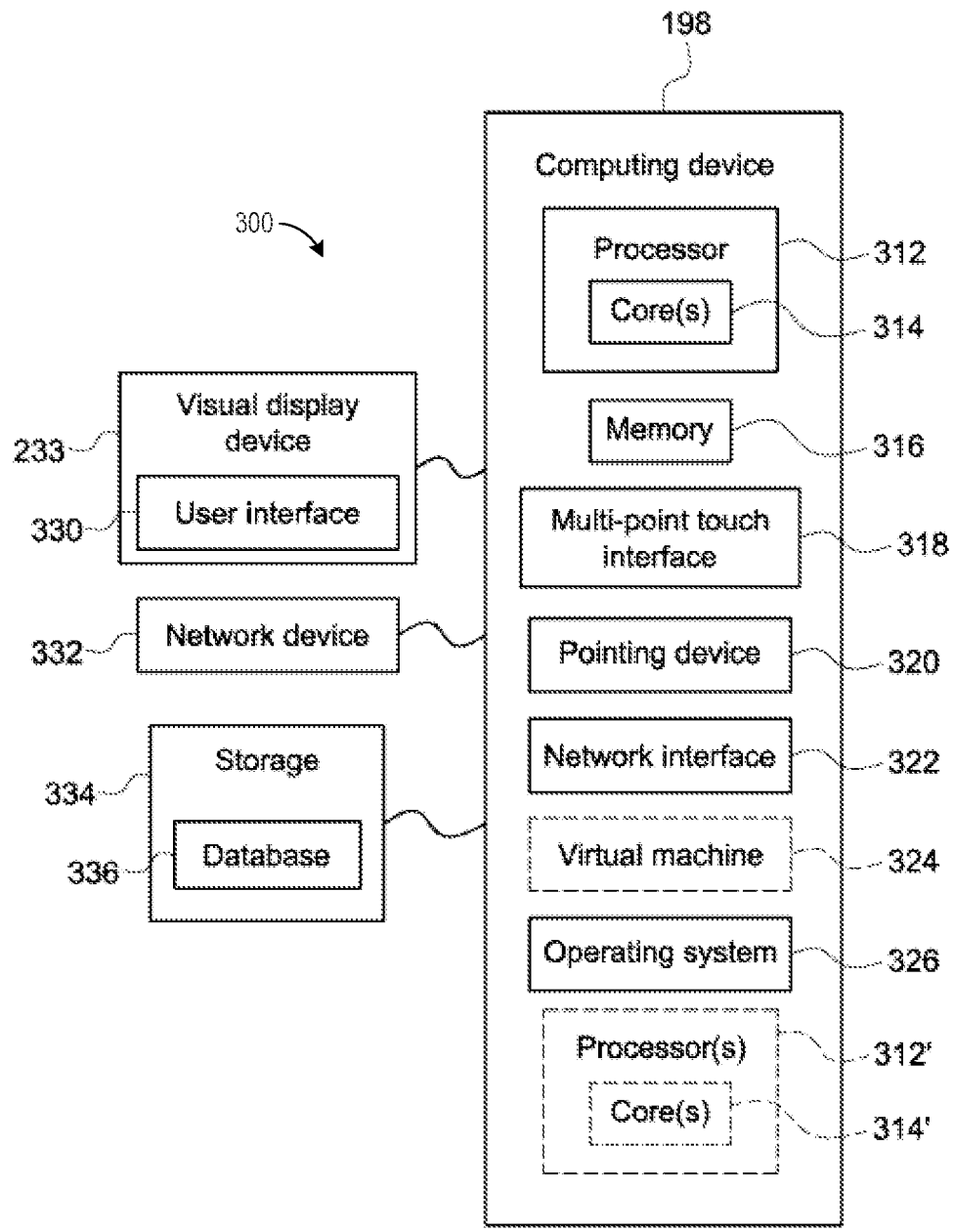
FIG. 3 is an exemplary computing device which may be programmed and/or configured to operate, for example, the system of FIGS. 1A and/or 1B and may also be used to implement certain processes described in relation to various embodiments of the present disclosure.

In some embodiments, computer 198 shown in FIG. 1B may control the operation of the system 170 shown in FIG. 1A and may implement various aspects of the disclosed embodiments. FIG. 3 is a block diagram of an exemplary system 300, with computing device 198, that may be used in certain embodiments. The computing device 198 may include one or more non-transitory computer-readable media for storing one or more computer-executable instructions or software for implementing exemplary embodiments. The non-transitory computer-readable media may include, but are not limited to, one or more types of hardware memory, non-transitory tangible media (for example, one or more magnetic storage disks, one or more optical disks, one or more flash drives), and the like. For example, memory 316 included in the computing device 198 may store computer-readable and computer-executable instructions or software for interfacing with and/or controlling an operation of the scanner system 170. The computing device 198 may also include configurable and/or programmable processor 312 and associated core(s) 314, and optionally, one or more additional configurable and/or programmable processing devices, e.g., processor(s) 312' and associated core(s) 314' (for example, in the case of computer systems having multiple processors/cores), for executing computer-readable and computer-executable instructions or software stored in the memory 316 and other programs for controlling system hardware. Processor 312 and processor(s) 312' may each be a single core processor or multiple core (314 and 314') processor.

Virtualization may be employed in the computing device 198 so that infrastructure and resources in the computing device may be shared dynamically. A virtual machine 324 may be provided to handle a process running on multiple processors so that the process appears to be using only one computing resource rather than multiple computing resources. Multiple virtual machines may also be used with one processor.

Memory 316 may include a computer system memory or random access memory, such as DRAM, SRAM, EDO RAM, and the like. Memory 316 may include other types of memory as well, or combinations thereof.

A user may interact with the computing device 198 through a visual display device 233, such as a computer monitor, which may display one or more user interfaces 330 that may be provided in accordance with exemplary embodiments. Visual display device 233 may be the same as display system 204 shown in FIG. 1B in some embodiments. The computing device 198 may include other I/O devices for receiving input from a user, for example, a keyboard or any suitable multi-point touch interface 318, a pointing device 320 (e.g., a mouse). The interface 318 such as a keyboard and the pointing device 320 may be coupled to the visual display device 233. The computing device 198 may include other suitable conventional I/O peripherals.

The computing device 198 may also be connected to one or more storage devices 334, such as a hard-drive, CD-ROM, or other computer readable media, for storing data and computer-readable instructions and/or software that interface with and/or control an operation of the scanner system 170 shown in FIG. 1A described herein and/or to implement exemplary processes and methods described herein. Exemplary storage device 334 may also store one or more databases for storing any suitable information required to implement exemplary embodiments. For example, exemplary storage device 334 can store one or more databases 336 for storing information, such as scan sequences, X-ray data, X-ray images, photon counts, estimation of electrical properties, electrical property maps, and/or any other information that can be used to implement exemplary embodiments of the present invention. The databases may be updated manually or automatically at any suitable time to add, delete, and/or update one or more items in the databases.

The computing device 198 can include a network interface 322 configured to interface via one or more network devices 332 with one or more networks, for example, Local Area Network ("LAN"), Wide Area Network ("WAN") or the Internet through a variety of connections including, but not limited to, standard telephone lines, LAN or WAN links (for example, 802.11, T1, T3, 56 kb, X.25), broadband connections (for example, ISDN, Frame Relay, ATM), wireless connections, Controller Area Network ("CAN"), or some combination of any or all of the above. The network interface 322 may include a built-in network adapter, network interface card, PCMCIA network card, card bus network adapter, wireless network adapter, USB network adapter, modem or any other device suitable for interfacing the computing device 198 to any type of network capable of communication and performing the operations described herein. Moreover, the computing device 198 may be any computer system, such as a workstation, desktop computer, server, laptop, handheld computer, tablet computer, or other form of computing or telecommunications device that is capable of communication and that has sufficient processor power and memory capacity to perform the operations described herein.

The computing device 198 may run any operating system 326, such as any of the versions of the Microsoft® Windows® operating systems, the different releases of the Unix and Linux operating systems, any version of the MacOS® for Macintosh computers, any embedded operating system, any real-time operating system, any open-source operating system, any proprietary operating system, or any other operating system capable of running on the computing device and performing the operations described herein. In exemplary embodiments, the operating system 326 may be run in native mode or emulated mode. In an exemplary embodiment, the operating system 326 may be run on one or more cloud machine instances.

In exemplary embodiments, the CT system 170 shown in FIG. 1A can be configured and/or programmed to transmit instructions, commands, and/or requests to the computing device 198 to control the CT components to perform scan sequences and can be programmed and/or configured to receive CT projection data or CT images from the computing device 198.

Figure 4:
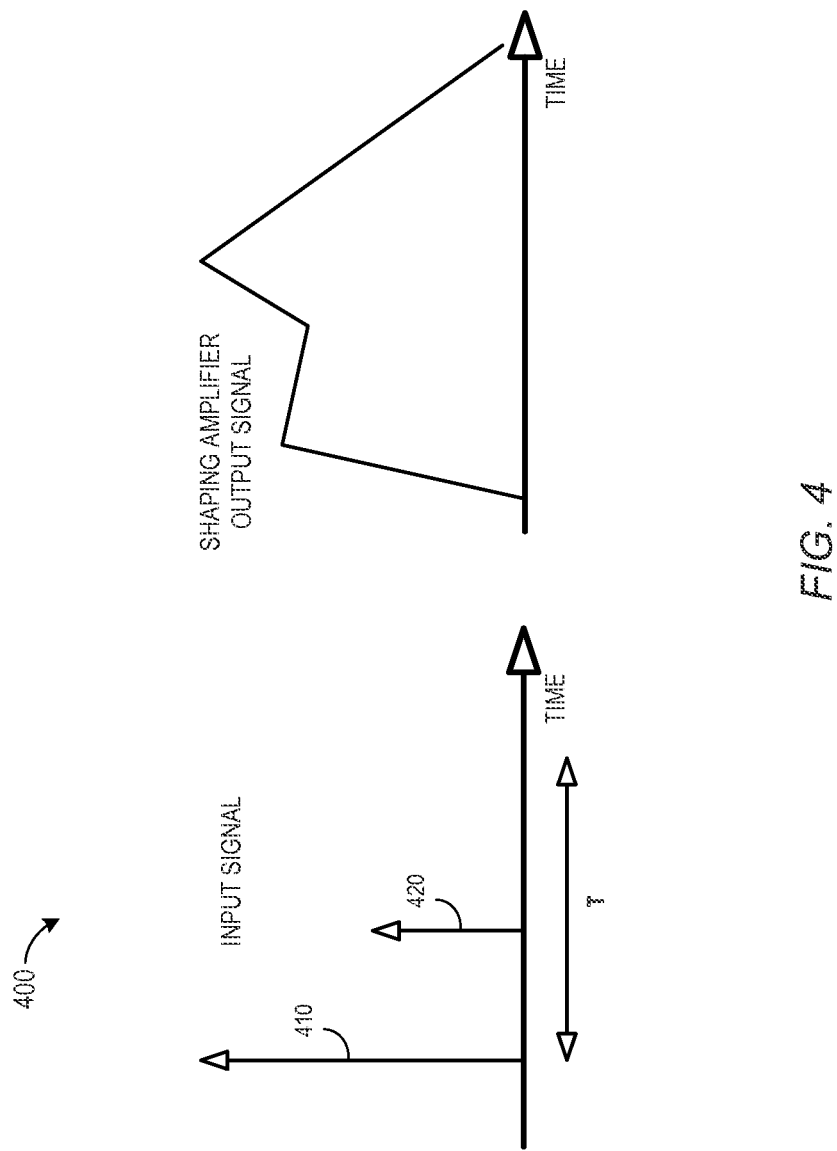
FIG. 4 illustrates an output of a relatively slow shaper.

FIG. 4 illustrates 400 an output of a relatively slow shaper (associated with collection time $\tau_s$) when photons associated with two events 410, 420 comprise an input signal. Note that that shaping amplifier output signal might reflect a correct total amount of energy ($E_{TOTAL}$) but the photon count associated with each interval may be unknown. Note that an output of a relatively fast shaper (associated with collection time $\tau_f$)—when photons associated with two events comprise an input signal—might be combined with information from a slow shaper, such as via a statistical algorithm. Moreover, such an approach might provide an accurate count of detected photons for the detector. That is, the energy associated with each event might be known, providing for an improved quality of an X-ray or CT image.

According to some embodiments described herein, pile-up events in a photon-counting (semiconductor) detector may be corrected by applying fast shaping circuitry having a characteristic time based on the detector weighting potential profile, applied electric field, and semiconductor material properties (such as electron and hole mobilities). A typical (slow) shaper (with time constant $\tau_s$ of approximately 160-500 ns) may accurately estimate the total energy with complete collection of the induced charge contributed by both electron and hole motion. The fast shaper (with time constant $\tau_f$ of approximately 10-40 ns) may accurately estimate the charge contribution of an electron cloud approaching the anode, helping determine the count information even at high flux rate. The results from the fast and slow shaper may be, for example, combined using a statistical algorithm to retrieve the photon count, and thus energy information.

Figure 5:
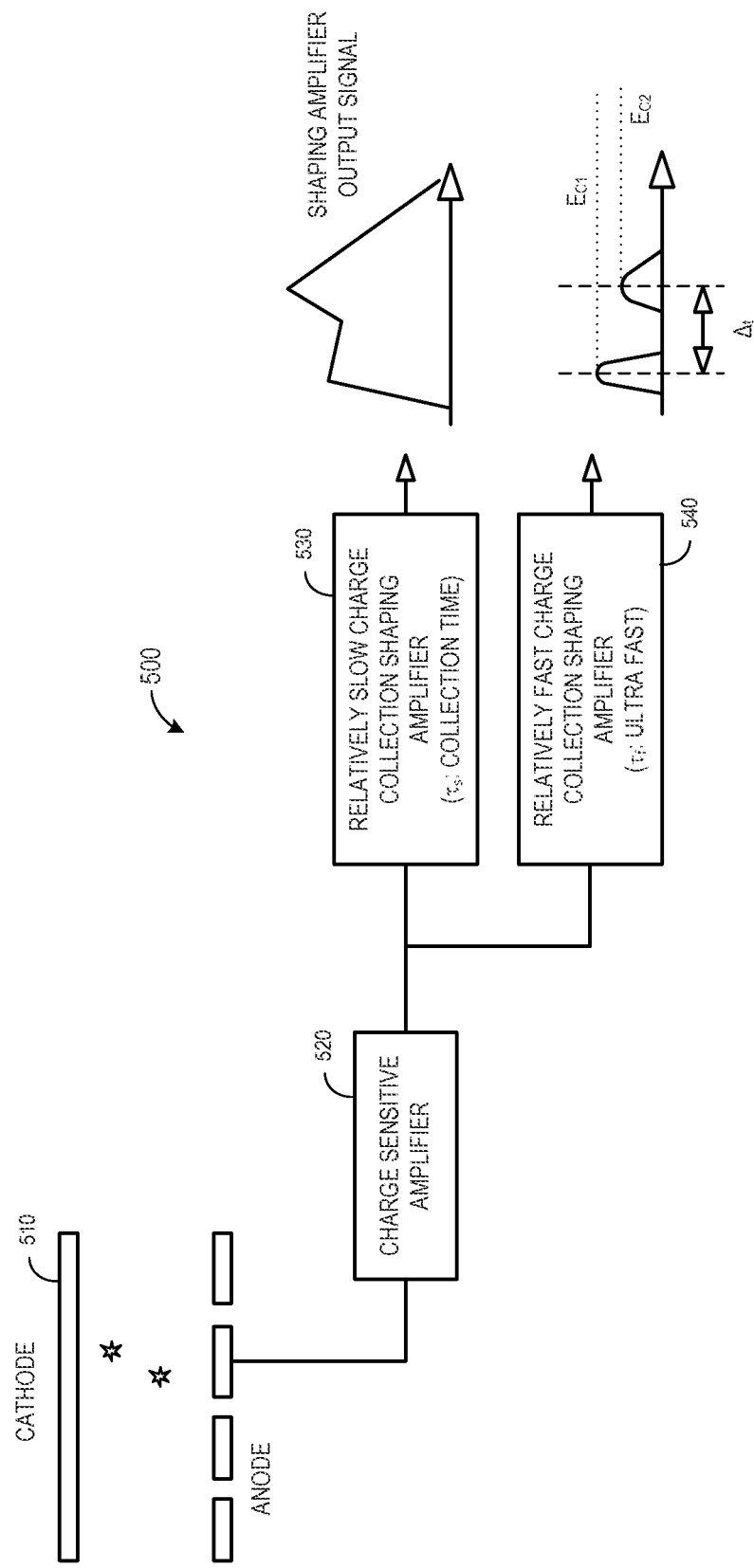
FIG. 5 is a system in accordance with some embodiments.

FIG. 5 is a system 500 in accordance with some embodiments. The system 500 includes a photon-counting detector 510, such as a Cadmium Zinc Telluride ("CZT") or Cadmium Telluride (CdTe) detector having a cathode and anode that outputs a signal to a charge sensitive amplifier 520. The output of the charge sensitive amplifier 520 may be provided to, according to some embodiments, a relatively slow charge collection shaping amplifier 530 and a relatively fast charge collection shaping amplifier 540. The relatively fast charge collection shaping amplifier 540 may comprise, for example, an ultra-fast shaper (a specifically designed high-bandwidth, band-pass filter) signal to recover more accurately the both count and energy information of pile-up events, while the standard (slow) shaper (a low-bandwidth, band-pass filter) provides an estimate of the total energy $E_{TOTAL}$ (collecting all induced charge).

Some embodiments described herein use the fast shaper signal, which could provide the accurate pileup information at high flux rate. In the meantime, the energy information is recorded by the slow shaper signal with complete charge collection. Therefore, such an approach may correct for the pile-up events without compromising the energy resolution (that is $E_{C1}$ associated with a first event and $E_{C2}$ associated with a second event may be determined). Moreover, embodiments described herein provide a simple and cost-effective solution for correcting pile-up events, thereby improving X-ray and CT image quality.

Figure 6:
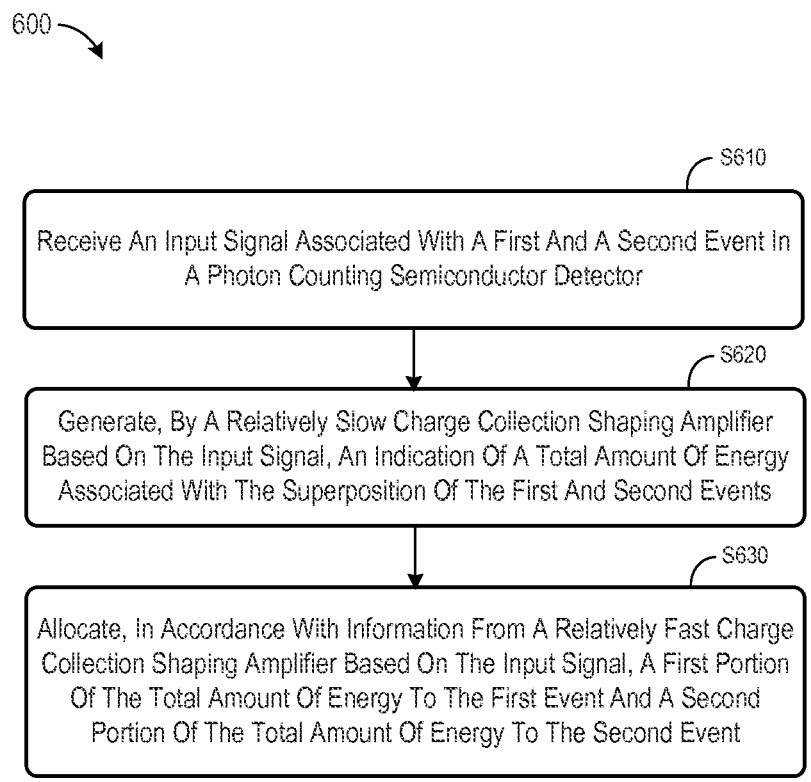
FIG. 6 is a flow chart of a method associated with some embodiments.

FIG. 6 is a flow chart of a method 600 in accordance with some embodiments. The flow charts described herein do not imply a fixed order to the steps, and embodiments of the present invention may be practiced in any order that is practicable. Note that any of the methods described herein may be performed by hardware, software, or any combination of these approaches. For example, a computer-readable storage medium may store thereon instructions that when executed by a machine result in performance according to any of the embodiments described herein.

At S610, an input signal associated with superposition of a first and a second event in a photon-counting semiconductor detector may be received. The input signal may be received, for example, via a charge sensitive amplifier coupled to the photon-counting semiconductor detector.

At S620, a relatively slow charge collection shaping amplifier (e.g., having a time constant of substantially or approximately from 160 ns to 200 ns) may receive the input signal and generate an indication of a total combined energy associated with the first and second events. The relatively slow charge collection shaping amplifier might comprise, for example, a low-bandwidth, band-pass filter. According to some embodiments, a relatively slow charge collection shaping amplifier might have a time constant of from substantially 160 ns to substantially 500 ns and the relatively fast charge collection shaping amplifier might have a time constant of substantially 10 to substantially 40 ns. In some cases, the time constants of slow and fast shaping amplifiers are characterized by a detector weighting potential profile, applied electric field, and semiconductor material properties (such as electron and hole mobilities). The slow shaper time constant may allow for complete collection of the induced charge contributed by both electron and hole motion, and may be longer than the electron drift time crossing the whole detector from cathode to anode. The fast shaper time constant may be characterized by the drift of the electron cloud only approaching the anode.

A relatively fast charge collection shaping amplifier (e.g., having a time constant of substantially 10-40 ns) may receive the input signal and generate an indication that is used at S630 to allocate a first portion of the total amount of energy to the first event and a second portion of the total amount of energy to the second event.

Figure 7:
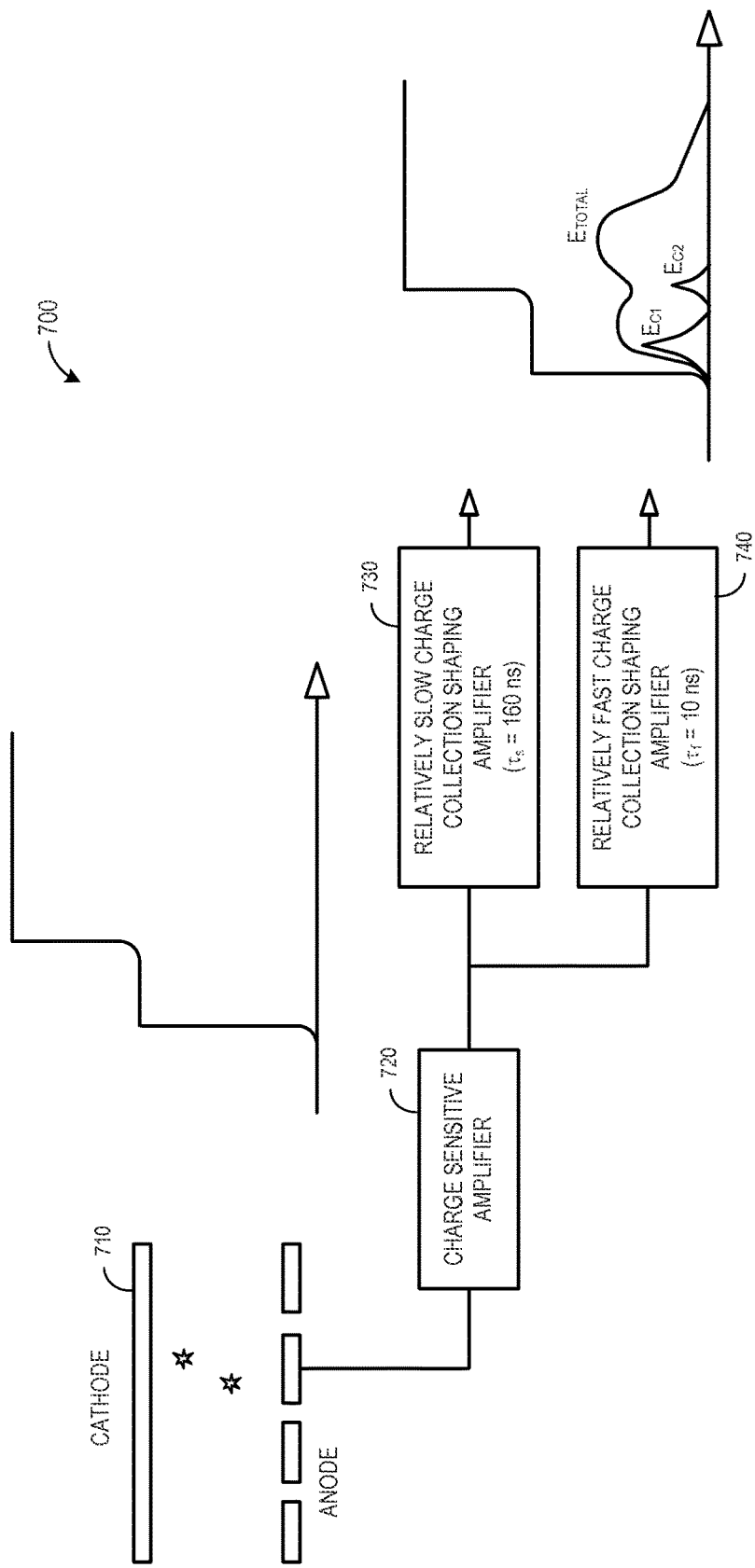
FIG. 7 illustrates simulation results according to some embodiments.

FIG. 7 illustrates simulation results 700 according to some embodiments. The results 700 might be associated with, for example, a CZT detector 710 having a pixel size of 600 um and a thickness of 5 mm. Moreover, the arrival of two X-ray photons might be simulated: an 80 keV photon followed by 60 keV photon 300 ns later. As can be seen, the overall induced charge and information at the charge sensitive amplifier 720 may be output from a relatively slow charge collection shaping amplifier 730 as an accurate estimation of the total energy, $E_{TOTAL}$. Moreover, a relatively fast charge collection shaping amplifier 740 may accurately allocate percentages of the total energy to each photon, $E_{C1}$ and $E_{C2}$.

There may be several different way to use the fast shaper (specifically-designed high-bandwidth, band-pass filter) signal to accurately recover energy information of pile-up events, while the standard slow shaper (charge integrator) provides the total energy, $E_{TOTAL}$ (collecting all induced charge). Three different approaches will now be described in connection with FIGS. 8 through 10:

- A Multiple-Threshold Mode: the fast shaper works with multiple thresholds. For example, the first threshold may enable rejection of signals pertaining to low-energy flux (noise); the second threshold may enable separation of the estimated photon energy into low- and high-energy allocations. Note that the total energy from the slow shaper might be used as a constraint when allocating the particular photons to the corresponding energy bins to improve accuracy.
- A Peak ADC Mode: measure the amplitude of 2 separate signals ($E_{C1}$ and $E_{C2}$) in fast shaper channel, and then use the energy ratio to recover the energy (E1 and E2) of two events from the standard slow shaper channel, which characterizes the total energy, $E_{TOTAL}$.
- A Time Correction Mode: the time difference $\Delta t$ of fast signals is also recorded and then used to analytically calculate the waveform of the signal, and recover the energy information at a high resolution.

Figure 8:
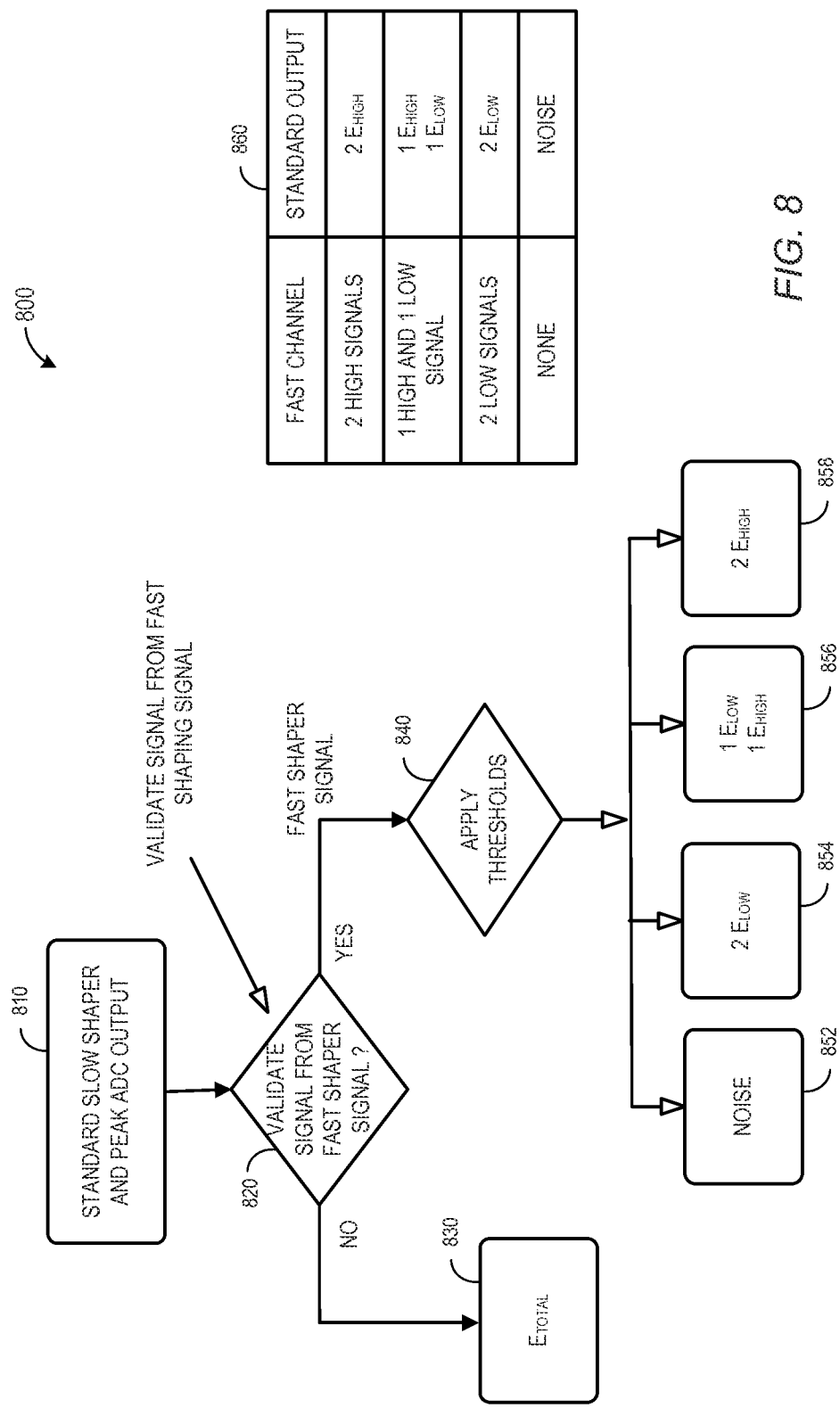
FIG. 8 illustrates a multi-bin embodiment in accordance with some embodiments.

In the "multiple-threshold mode," a relatively fast charge collection shaping amplifier (high-bandwidth, band-pass filter) may record a photon in one of a plurality of energy bins based on an energy threshold, and the number of photons in each bin is then used to allocate the first portion of the total amount of energy to the first event and the second portion of the total amount of energy to the second event. FIG. 8 illustrates a multi-bin embodiment 800 in accordance with some embodiments. In this embodiment, standard slow shaper and ADC or Charge-to Digital Convertor ("QDC") output at 810 are used, along with validation of the signal from a fast shaper signal, to determine if there was a pile-up condition at 820. If there was no pile up, all of the energy ($E_{TOTAL}$) is associated with a single event at 830.

If there was a pile-up condition at 820, thresholds may be applied at 840 and a photon might be assigned to one of a number of bins. For example, in the case of pile-up, the two photons (corresponding to the two recorded events) might be allocated to low- and high-energy bins based on a series of energy thresholds in the fast shaping circuitry. The fast shaping circuitry may work with multiple thresholds (bins): (1) a first threshold 852 to reject the low-energy flux (noise); (2) a second threshold to help separate the estimated photon energy into low- and high-energy components. Note that the total energy from the slow shaper still can be used as a constraint when allocating the particular photons to the corresponding energy bins to improve the accuracy.

In the example of FIG. 8, three additional bins are utilized in addition to the noise bin 852: (1) a bin 854 indicating that 2 low-energy photons (2 $E_{LOW}$) were received; (2) a bin 856 indicating that one high-energy photon (1 $E_{HIGH}$) and one low-energy photon (1 $E_{LOW}$) were received; and (3) a bin 858 indicating that 2 high-energy photons (2 $E_{HIGH}$) were received. Note that the fast channel may be mapped to standard output as illustrated by table 860.

Figure 9:
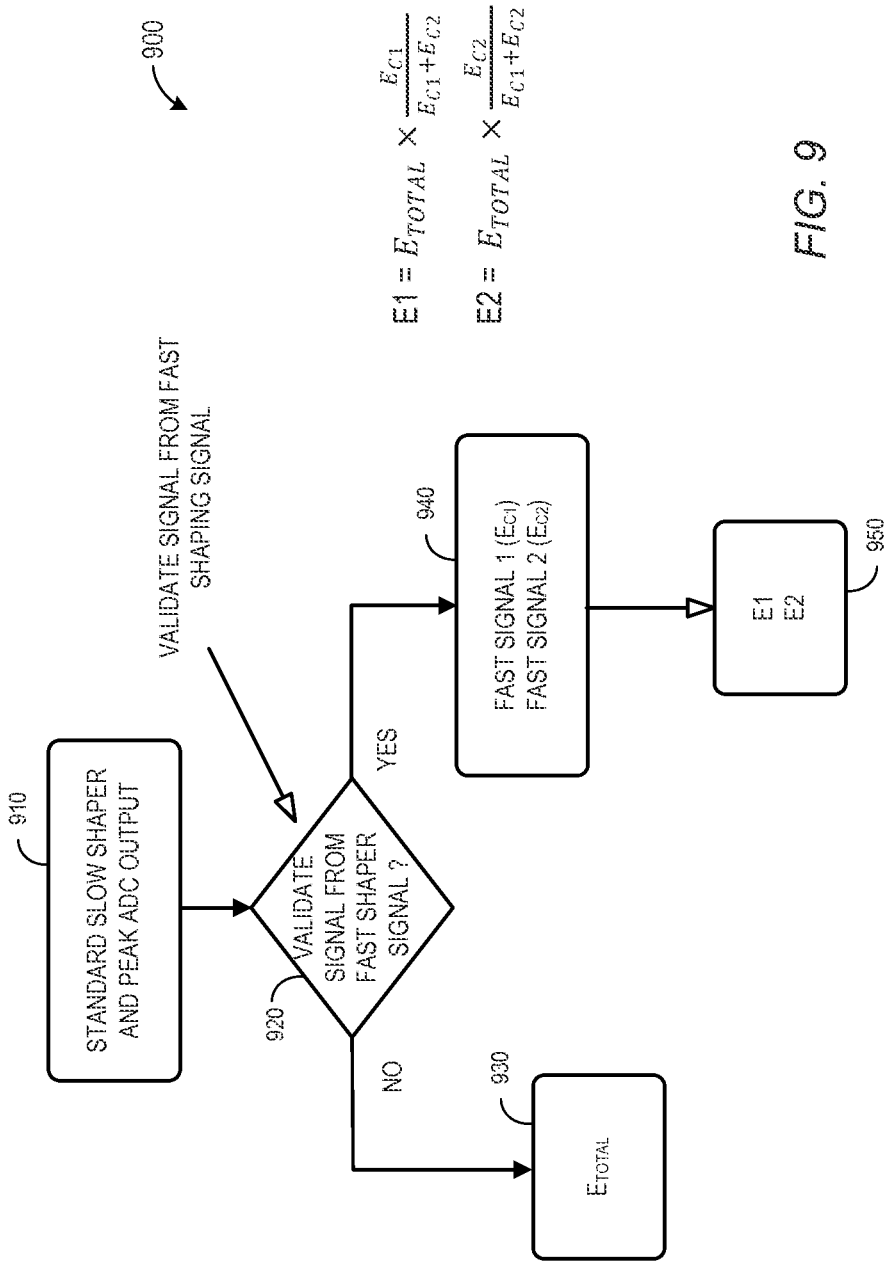
FIG. 9 illustrates a peak Analog-to-Digital Converter ("ADC") embodiment according to some embodiments.

In the "peak ADC mode," a relatively fast charge collection shaping amplifier may measure a first amplitude associated with a first event using a peak analog-to-digital converter and measure a second amplitude associated with the second event using a peak analog-to-digital converter. FIG. 9 illustrates a peak ADC (or QDC) embodiment 900 according to some embodiments. In this embodiment 900, standard slow shaper and peak ADC output (or QDC) at 910 are used, along with validation of the signal from a fast shaper signal, to determine if there was a pile-up condition at 920. If there was no pile up, all of the energy ($E_{TOTAL}$) is associated with a single event at 930.

If there was a pile-up condition at 920, the amplitude of two separate signals ($E_{C1}$ and $E_{C2}$) in the fast shaper channel are measured with a peak ADC. The energy ratio of those signals may be used to recover the energy, E1 and E2, of the two events (photons). Again, the total energy from the standard slow shaper ($E_{TOTAL}$) may be utilized to calibrate the two signals to the correct energy levels. Note that in the ADC mode, the system may also use the energy difference from the fast shaper to restore the signal in the case of pile-up. Note that the allocation energy to each event might be performed as follows:

$$E1 = E_{TOTAL} \times \frac{E_{C1}}{E_{C1} + E_{C2}},$$

and $$E2 = E_{TOTAL} \times \frac{E_{C2}}{E_{C1} + E_{C2}}.$$

Figure 10:
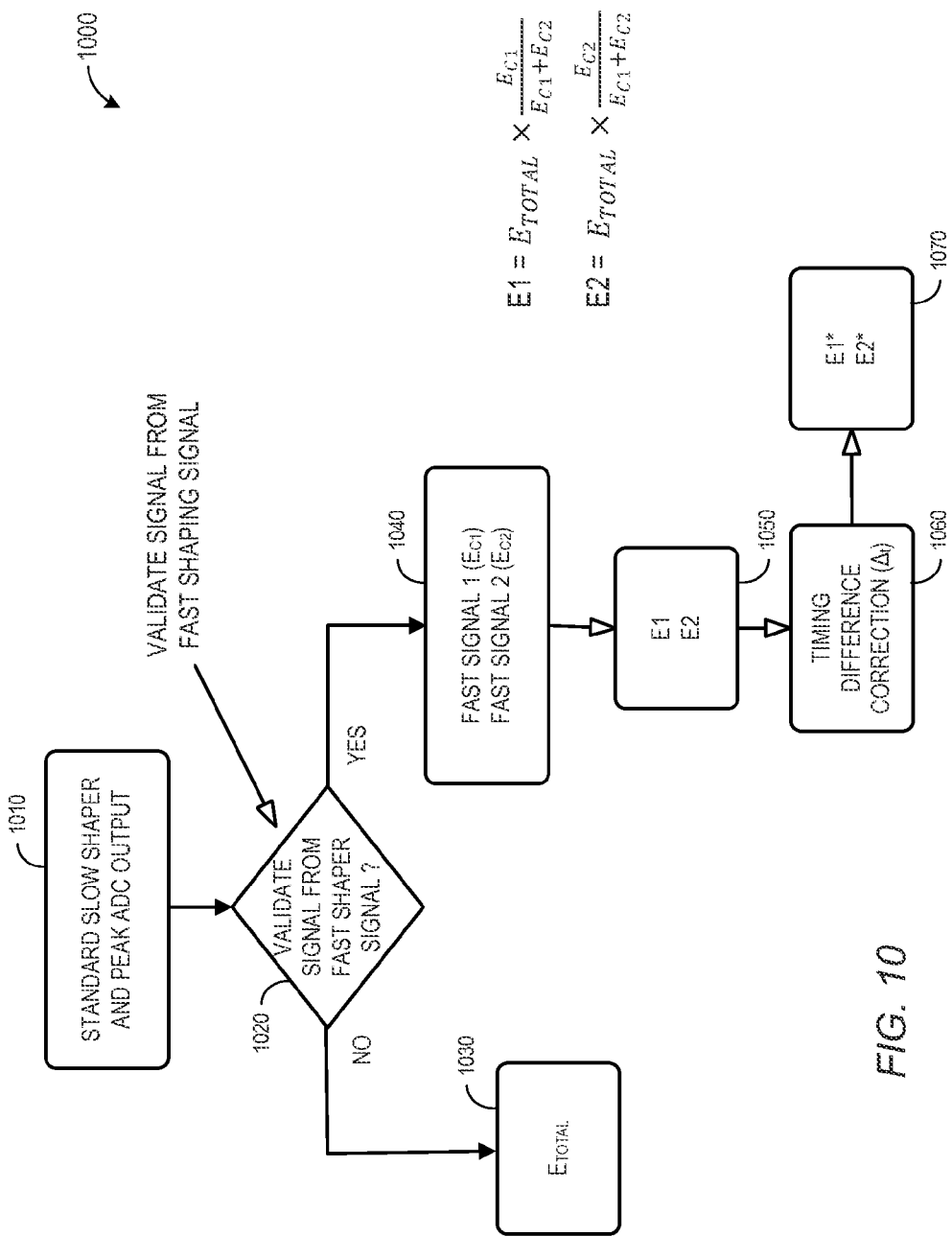
FIG. 10 illustrates an embodiment utilizing a timing difference correction in accordance with some embodiments.

In the "time correction mode," a first timing value may be recorded in connection with the first event and a second timing value may be recorded in connection with the second event, and the allocation of $E_{TOTAL}$ is further apportioned based on the first and second timing values. For example, the difference between the two time values may be used to apply a second-order correction on the signal. FIG. 10 illustrates an embodiment 1000 utilizing a timing difference correction in accordance with some embodiments. As before, standard slow shaper and ADC (or QDC) output at 1010 are used, along with validation of the signal from a fast shaper signal, to determine if there was a pile-up condition at 1020. If there was no pile up, all of the energy ($E_{TOTAL}$) is associated with a single event at 1030. Moreover, the two fast signals are used to allocate E1 and E2 at 1040 and 1050 as described with respect to steps 940 and 950 in FIG. 9.

According to some embodiments, this mode adds extra hardware capability to record the time difference in the fast shaper signal. In such a "fully-working" mode, for example, not only the energy level but also the time difference of the fast signals is recorded. The information is then used to analytically restore the waveform of the signal, and recover the energy information with higher accuracy. It should also be noted that this approach might have a higher cost due to the extra hardware requirement. In general, after the time difference correction value $\Delta_t$ is measured at 1060, it can be used to correct energy values E1* and E2* as follows:

$$E1^* = E1^* f(E1, E2, \Delta_t), \text{ and}$$

$$E2^* = E2^* f(E1, E2, \Delta_t).$$

Thus, some embodiments may add a fast shaper to guide counting, giving a high-count rate and good energy resolution at a reasonable cost, making it more practical to implement than other approaches.

It is to be understood that not necessarily all such objects or advantages described above may be achieved in accordance with any particular embodiment. Thus, for example, those skilled in the art will recognize that the systems and techniques described herein may be embodied or carried out in a manner that achieves or optimizes one advantage or group of advantages as taught herein without necessarily achieving other objects or advantages as may be taught or suggested herein.

For example, embodiments may be used to provide benefits in many medical imaging situations. One application may be to correct an edge effect in a photon-counting CT. In photon-counting CT, X-rays passing through the edge of an object tend to have a higher flux rate when the object and a bow-tie filter (dedicated to balance flux across detector channels) are not perfectly matched. In fact, when an object has an elliptical shape it may not be possible for the bow-tie filter and object to match perfectly from all projection angles. Therefore, the pile-up effect in the detector channels corresponding to these high flux X-rays can pose a great challenge to achieve diagnostic image quality. Such a situation can, for example, cause streaks, shading, and bias in the reconstructed CT values if not corrected properly (which can be done, for example, using embodiments described herein).

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A system, comprising:
    a detection system comprising a photon-counting semiconductor detector, configured to receive an input signal associated with a first event and a second event;
    a relatively slow charge collection shaping amplifier configured to receive the input signal and to output an indication of a total amount of energy associated with a combination of the first event and the second event; and
    a relatively fast charge collection shaping amplifier configured to receive the input signal and further configured to output an indication that is used to allocate a first portion of the total amount of energy to the first event and a second portion of the total amount of energy to the second event.

2. The system of claim 1, wherein the relatively slow charge collection shaping amplifier has a first time constant and the relatively fast charge collection shaping amplifier has a second time constant, the first time constant and second time constant being characterized by at least one of: (i) a detector weighting potential profile, (ii) an applied electric field, and (iii) semiconductor material properties.

3. The system of claim 2, wherein the relatively slow charge collection shaping amplifier comprises a low-bandwidth, band-pass filter, and the relatively fast charge collection shaping amplifier comprises a high-bandwidth, band-pass filter.

4. The system of claim 1, further comprising a charge sensitive amplifier configured to receive the input signal, wherein the charge sensitive amplifier is coupled to the photon-counting semiconductor detector.

5. The system of claim 1, wherein the relatively fast charge collection shaping amplifier is configured to: record a photon count in one of a plurality of bins based on an energy threshold, and further configured to use a number of photons in each bin of the plurality of bins to allocate the first portion of the total amount of energy to the first event and the second portion of the total amount of energy to the second event.

6. The system of claim 5, wherein the plurality of bins include: (i) a noise bin, (ii) a low-energy bin, and (iii) a high-energy bin.

7. The system of claim 1, wherein the relatively fast charge collection shaping amplifier comprises a peak analog-to-digital converter or a charge-to-digital converter and is configured to: measure a first amplitude value associated with the first event using the peak analog-to-digital converter or the charge-to-digital converter, measure a second amplitude value associated with the second event using the peak analog-to-digital converter or the charge-to-digital converter, and allocate the total amount of energy to the first event and the second event based on the first amplitude value and the second amplitude value.

8. A method, comprising:
    receiving an input signal associated with a first event and a second event in a photon-counting semiconductor detector;
    generating, by a relatively slow charge collection shaping amplifier based on the input signal, an indication of a total amount of energy associated with the first event and the second event; and
    allocating, in accordance with information from a relatively fast charge collection shaping amplifier based on the input signal, a first portion of the total amount of energy to the first event and a second portion of the total amount of energy to the second event.

9. The method of claim 8, wherein the relatively slow charge collection shaping amplifier comprises a low-bandwidth, band-pass filter having a first time constant and the relatively fast charge collection shaping amplifier comprises a high-bandwidth, band-pass filter having a second time constant.

10. The method of claim 9, wherein the first time constant and the second time constant are characterized by at least one of: (i) a detector weighting potential profile, (ii) an applied electric field, and (iii) semiconductor material properties.

11. The method of claim 8, further comprising recording a photon in one of a plurality of bins based on an energy threshold with the relatively fast charge collection shaping amplifier, and allocating the first portion of the total amount of energy to the first event and the second portion of the total amount of energy to the second event using a number of photons in each bin of the plurality of bins, wherein the plurality of bins include: (i) a noise bin, (ii) a low energy bin, and (iii) a high energy bin.

12. The method of claim 8, further comprising measuring a first amplitude value associated with the first event using a peak analog-to-digital converter or a charge-to-digital converter, measuring a second amplitude value associated with the second event using the peak analog-to-digital converter or the charge-to-digital converter, and allocating the total amount of energy to the first event and the second event based on the first amplitude value and the second amplitude value.

13. The method of claim 12, further comprising recording a first timing value in connection with the first event, recording a second timing value in connection with the second event, and correcting an allocation of the total amount of energy based on the first timing value and the second timing value.

14. An imaging system, comprising:
- an X-ray source configured to transmit X-rays toward an object;
- a photon-counting semiconductor detector configured to detect the X-rays traversing the object and to generate a detector signal associated with a first event and a second event;
- a charge sensitive amplifier configured to receive the detector signal and generate an output signal based on the detector signal;
- a relatively slow charge collection shaping amplifier configured to receive the output signal from the charge sensitive amplifier and to output an indication of a total amount of energy associated with a combination of the first event and the second event; and
- a relatively fast charge collection shaping amplifier configured to receive the output signal from the charge sensitive amplifier and to output an indication that is used to allocate a first portion of the total amount of energy to the first event and a second portion of the total amount of energy to the second event.

15. The imaging system of claim 14, wherein the relatively slow charge collection shaping amplifier comprises a low-bandwidth, band-pass filter having a first time constant and the relatively fast charge collection shaping amplifier comprises a high-bandwidth, band-bass filter having a second time constant.

16. The system of claim 15, wherein the first time constant and the second time constant are characterized by at least one of: (i) a detector weighting potential profile, (ii) an applied electric field, and (iii) semiconductor material properties.

17. The imaging system of claim 14, wherein the relatively fast charge collection shaping amplifier records a photon in one of a plurality of bins based on an energy threshold, and a number of photons in each bin of the plurality of bins is then used to allocate the first portion of the total amount of energy to the first event and the second portion of the total amount of energy to the second event, and further wherein the plurality of bins include: (i) a noise bin, (ii) a low-energy bin, and (iii) a high-energy bin.

18. The imaging system of claim 14, wherein the relatively fast charge collection shaping amplifier comprises a peak analog-to-digital converter, wherein the relatively fast charge collection shaping amplifier measures a first amplitude value associated with the first event using the peak analog-to-digital converter, and measures a second amplitude value associated with the second event using the peak analog-to-digital converter, and an allocation of the total amount of energy to the first event and the second event is based on the first amplitude value and the second amplitude value.

* * * * *